(12) United States Patent
Rothschild et al.

(10) Patent No.: US 7,534,861 B2
(45) Date of Patent: May 19, 2009

(54) COMPOSITIONS AND METHODS FOR IMMUNOAFFINITY PURIFICATION

(75) Inventors: Kenneth J. Rothschild, Newton, MA (US); Sadanand Gite, Cambridge, MA (US); Jerzy Olejnik, Allston, MA (US); Mark Lim, Reading, MA (US)

(73) Assignee: Ambergen, Inc., Watertown, MA (US)

( * ) Notice: Subject to any disclaimer, the term of this patent is extended or adjusted under 35 U.S.C. 154(b) by 512 days.

(21) Appl. No.: 10/340,179

(22) Filed: Jan. 10, 2003

(65) Prior Publication Data

US 2004/0138413 A1   Jul. 15, 2004

(51) Int. Cl.
*C07K 14/00* (2006.01)
*C12N 15/00* (2006.01)

(52) U.S. Cl. .................. 530/350; 530/300; 530/402; 435/320.1; 435/69.1; 435/70.1

(58) Field of Classification Search .......... 536/24.3; 435/325, 320.1
See application file for complete search history.

(56) References Cited

U.S. PATENT DOCUMENTS

| | | | | |
|---|---|---|---|---|
| 5,641,657 A | * | 6/1997 | Ruben et al. | 435/69.52 |
| 5,770,377 A | * | 6/1998 | Picksley et al. | 435/7.1 |
| 6,017,735 A | * | 1/2000 | O'Hare et al. | 435/69.7 |
| 6,326,464 B1 | * | 12/2001 | Conseiller et al. | 530/324 |
| 2004/0181048 A1 | * | 9/2004 | Wang | 536/24.3 |

FOREIGN PATENT DOCUMENTS

FR   WO9704092   *   2/1997

OTHER PUBLICATIONS

Phelan A, Elliott G, O'Hare P Intercellular delivery of functional p53 by the herpesvirus protein VP22. Nat Biotechnol. May 1998;16(5):440-3.*
EST Database ID No. CNS07SIY.*
Invitrogen expression vector, pEF4/His A, B, C., Catalog No. V943-20, Apr. 22, 2002.*
Stephen et al., JMB, vol. 248, p. 58-78, 1995.*

* cited by examiner

*Primary Examiner*—Larry R. Helms
*Assistant Examiner*—Lei Yao
(74) *Attorney, Agent, or Firm*—Medlen & Carroll, LLP

(57) ABSTRACT

A hybrid polypeptide composed of a p53 epitope peptide and a desired functional protein are produced by recombinant DNA techniques. A DNA expression vector is constructed that includes segments of DNA coding for the epitope peptide and the desired functional protein. An optional linking portion is contemplated. The linking portion of the epitope peptide is cleavable at a specific amino acid residue adjacent the functional protein by use of a sequence specific proteolytic enzyme or chemical proteolytic agent. The hybrid polypeptide expressed by the host cells transformed by the cloning vector is removed therefrom and purified by affinity chromatography techniques by use of an immobilized antibody specific to the antigenic portion of the epitope peptide. The protein is then cleaved from the isolated hybrid polypeptide with an appropriate proteolic enzyme or chemical agent, thereby releasing the mature functional protein in highly purified, highly active state.

13 Claims, 3 Drawing Sheets

```
  1 meepqsdpsv epplsqetfs dlwkllpenn vlsplpsqam ddlmlspddi eqwftedpgp
 61 deaprmpeaa prvapapaap tpaapapaps wplsssvpsq ktyqgsygfr lgflhsgtak
121 svtctyspal nkmfcqlakt cpvqlwvdst pppgtrvram aiykqsqhmt evvrrcphhe
181 rcsdsdglap pqhlirvegn lrveylddrn tfrhsvvvpy eppevgsdct tihynymcns
241 scmggmnrrp iltiitleds sgnllgrnsf evrvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd
```

Figure 1

```
   1 ccacctgaag tccaaaaagg gtcagtctac ctcccgccat aaaaaactca tgttcaagac
  61 agaagggcct gactcagact gacattctcc acttcttgtt ccccactgac agcctcccac
 121 ccccatctct ccctcccctg ccattttggg ttttgggtct ttgaacccut gcttgcaata
 181 ggtgtgcgtc agaagcaccc aggacttcca tttgctttgt cccggggctc cactgaacaa
 241 gttggcctgc actggtgttt tgttgtgggg aggaggatgg ggagtaggac ataccagctt
 301 agattttaag gtttttactg tgagggatgt ttgggagatg taagaaatgt tcttgcagtt
 361 aagggttagt ttacaatcag ccacattcta ggtaggggcc cacttcaccg tactaaccag
 421 ggaagctgtc cctcactgtt gaattttctc taacttcaag gcccatatct gtgaaatgct
 481 ggcatttgca cctacctcac agagtgcatt gtgagggtta atgaaataat gtacatctgg
 541 ccttgaaacc acctttatt acatgggtc tagaacttga ccccttgag ggtgcttgtt
 601 ccctctccct gttggtcggt gggttggtag tttctacagt tgggcagctg gttaggtaga
 661 gggagttgtc aagtctctgc tggcccagcc aaaccctgtc tgacaacctc ttggtgaacc
 721 ttagtaccta aaaggaaatc tcacccaatc ccacaccctg gaggatttca tctcttgtat
 781 atgatgatct ggatccacca agacttgttt tatgctcagg gtcaatttct tttttctttt
 841 tttttttttt tttcttttc tttgagactg ggtctcgctt tgttgcccag gctggagtgg
 901 agtggcgtga tcttggctta ctgcagcctt gcctcccccg gctcgagcag tcctgcctca
 961 gcctccggag tagctgggac cacaggttca tgccaccatg gccagccaac ttttgcatgt
1021 tttgtagaga tggggtctca cagtgttgcc caggctggtc tcaaactcct gggctcaggc
1081 gatccacctg tctcagcctc ccagagtgct gggattacaa ttgtgagcca ccacgtccag
1141 ctggaagggt caacatcttt tacattctgc aagcacatct gcatttcac cccacccttc
1201 ccctccttct ccctttttat atcccatttt tatatcgatc tcttatttta caataaaact
1261 ttgctgccac ctgtgtgtct gaggggtg
```

Figure 2

SEQUENCE LISTING

```
<160> NUMBER OF SEQ ID NOS: 36

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Thr Phe Ser Asp Leu Trp Lys Leu Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Thr Phe Ser Asp Leu Trp Lys Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Phe Ser Asp Leu Trp Lys Leu Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Thr Phe Ser Asp Leu His Lys Leu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Thr Phe Ser Asp Leu Tyr Lys Leu Leu
1               5

<210> SEQ ID NO 6
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 6

Thr Phe Ser Asp Leu Gly Lys Leu Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Thr Phe Ser Asp Leu Asn Lys Leu Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Thr Phe Ser Asp Leu Phe Lys Leu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Thr Phe Ser Asp Leu Asp Lys Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Thr Phe Ser Asp Leu Thr Lys Leu Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Glu Thr Phe Ser Asp Leu His Lys Leu Leu
1               5                   10

<210> SEQ ID NO 12
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 12

Gln Glu Thr Phe Ser Asp Leu His Lys Leu Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Ser Gln Glu Thr Phe Ser Asp Leu His Lys Leu Leu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Leu Ser Gln Glu Thr Phe Ser Asp Leu His Lys Leu Leu
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Glu Thr Phe Ser Asp Leu His Lys Leu Leu Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Gln Glu Thr Phe Ser Asp Leu His Lys Leu Leu Pro
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic

<400> SEQUENCE: 17

Ser Gln Glu Thr Phe Ser Asp Leu His Lys Leu Leu Pro
1               5                   10

<210> SEQ ID NO 18
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 18

Leu Ser Gln Glu Thr Phe Ser Asp Leu His Lys Leu Leu Pro Glu
1               5                   10                  15

<210> SEQ ID NO 19
<211> LENGTH: 8
<212> TYPE: DNA
<213> ORGANISM: Artificial Sequence
<220> FEATURE:
<223> OTHER INFORMATION: Synthetic

<400> SEQUENCE: 19 taaggagg                                                                    8

<210> SEQ ID NO 20
<211> LENGTH: 393
<212> TYPE: PRT
<213> ORGANISM: Homo sapiens

<400> SEQUENCE: 20

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
```

```
                   275                 280                 285
Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                    340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 21
<211> LENGTH: 1288
<212> TYPE: DNA
<213> ORGANISM: Homo sapiens

<400> SEQUENCE: 21
ccacctgaag tccaaaaagg gtcagtctac ctcccgccat aaaaaactca tgttcaagac      60
agaagggcct gactcagact gacattctcc acttcttgtt ccccactgac agcctcccac    120
ccccatctct ccctcccctg ccatttttggg ttttgggtct ttgaacccctt gcttgcaata   180 ggtgtgcgtc agaagcaccc aggacttcca tttgctttgt cccggggctc cactgaacaa    240
gttggcctgc actggtgttt tgttgtgggg aggaggatgg ggagtaggac ataccagctt    300
agattttaag gttttttactg tgagggatgt ttgggagatg taagaaatgt tcttgcagtt    360
aagggttagt ttacaatcag ccacattcta ggtaggggcc cacttcaccg tactaaccag    420
ggaagctgtc cctcactgtt gaattttctc taacttcaag gcccatatct gtgaaatgct    480
ggcatttgca cctacctcac agagtgcatt gtgagggtta atgaaataat gtacatctgg    540
ccttgaaacc accttttatt acatgggggtc tagaacttga ccccccttgag ggtgcttgtt   600 ccctctccct gttggtcggt gggttggtag tttctacagt tgggcagctg gttaggtaga    660
gggagttgtc aagtctctgc tggcccagcc aaaccctgtc tgacaacctc ttggtgaacc    720
ttagtaccta aaaggaaatc tcaccccatc ccacaccctg gaggatttca tctcttgtat    780
atgatgatct ggatccacca agacttgttt tatgctcagg gtcaatttct ttttttcttt    840
tttttttttt tttctttttc tttgagactg ggtctcgctt tgttgcccag gctggagtgg    900
agtggcgtga tcttggctta ctgcagcctt tgcctccccg gctcgagcag tcctgcctca    960
gcctccggag tagctgggac acaggttca tgccaccatg gccagccaac ttttgcatgt    1020
tttgtagaga tgggggtctca cagtgttgcc caggctggtc tcaaactcct gggctcaggc   1080
gatccacctg tctcagcctc ccagagtgct gggattacaa ttgtgagcca ccacgtccag    1140
ctggaagggt caacatcttt tacattctgc aagcacatct gcattttcac ccacccttc    1200 ccctccttct ccctttttat atcccatttt tatatcgatc tcttatttta caataaaact    1260
ttgctgccac ctgtgtgtct gagggggtg                                      1288

<210> SEQ ID NO 22
<211> LENGTH: 27
<212> TYPE: DNA
```

```
<213> ORGANISM: Artificial Sequence
<220> FEATURE:
<223> OTHER INFORMATION: Synthetic

<400> SEQUENCE: 22
cagcagcttg tgcaggtcgc tgaaggt                                          27

<210> SEQ ID NO 23
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at this position can be any number of amino
      acids.

<400> SEQUENCE: 23

Xaa Asp Asp Asp Asp Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Asp Asp Asp Asp Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa at this position can be alanine, arginine,
      asparagine, aspartic acid, cysteine, glutamine, glutamic acid,
      glycine, histidine, isoleucine, leucine, lysine, methionine,
      phenylalanine, proline, serine, threonine, tyrosine, or valine.

<400> SEQUENCE: 25

Thr Phe Ser Asp Leu Xaa Lys Leu Leu
1               5

<210> SEQ ID NO 26
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Xaa at these positions can be any amino acids,
      and one to ten may be present or absent.
<220> FEATURE:
<221> NAME/KEY: MISC_FEATURE
<222> LOCATION: (16)..(16)
<223> OTHER INFORMATION: Xaa at this position can be alanine, arginine,
      asparagine, aspartic acid, cysteine, glutamine, glutamic acid,
      glycine, histidine, isoleucine, leucine, lysine, methionine,
      phenylalanine, proline, serine, threonine, tyrosine, or valine.
<220> FEATURE:
```

```
<221> NAME/KEY: MISC_FEATURE
<222> LOCATION: (20)..(29)
<223> OTHER INFORMATION: Xaa at these positions can be any amino acid,
      and one to ten may be present or absent.

<400> SEQUENCE: 26

Xaa Xaa Xaa Xaa Xaa Xaa Xaa Xaa Xaa Xaa Thr Phe Ser Asp Leu Xaa
1               5                   10                  15

Lys Leu Leu Xaa Xaa Xaa Xaa Xaa Xaa Xaa Xaa Xaa Xaa
            20                  25

<210> SEQ ID NO 27
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: Xaa at these positions can be any amino acid.
<220> FEATURE:
<221> NAME/KEY: MISC_FEATURE
<222> LOCATION: (6)..(6)
<223> OTHER INFORMATION: Xaa at this position can be any amino acid.

<400> SEQUENCE: 27

Xaa Xaa Xaa Xaa Lys Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: Xaa at these positions can be any amino acid.
<220> FEATURE:
<221> NAME/KEY: MISC_FEATURE
<222> LOCATION: (6)..(6)
<223> OTHER INFORMATION: Xaa at this position can be any amino acid.

<400> SEQUENCE: 28

Xaa Xaa Xaa Xaa Arg Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: Xaa at these positions can be any amino acid.
<220> FEATURE:
<221> NAME/KEY: MISC_FEATURE
<222> LOCATION: (6)..(6)
<223> OTHER INFORMATION: Xaa at this position can be any amino acid.

<400> SEQUENCE: 29

Xaa Xaa Xaa Xaa Gln Xaa
1               5

<210> SEQ ID NO 30
<211> LENGTH: 8
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: Xaa at these positions can be any amino acid.
<220> FEATURE:
<221> NAME/KEY: MISC_FEATURE
<222> LOCATION: (7)..(8)
<223> OTHER INFORMATION: Xaa at these positions can be any amino acid.

<400> SEQUENCE: 30

Xaa Xaa Xaa Xaa Xaa Pro Xaa Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: Xaa at these positions can be any amino acid.
<220> FEATURE:
<221> NAME/KEY: MISC_FEATURE
<222> LOCATION: (8)..(8)
<223> OTHER INFORMATION: Xaa at this position can be any amino acid.

<400> SEQUENCE: 31

Xaa Xaa Xaa Xaa Xaa Xaa Pro Xaa
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at this position can be glutamic acid or
     aspartic acid.

<400> SEQUENCE: 32

Ile Xaa Gly Arg
1

<210> SEQ ID NO 33
<211> LENGTH: 5
<212> TYPE: PRT
<213> ORGANISM: Artificial Sequence
<220> FEATURE:
<223> OTHER INFORMATION: Synthetic

<400> SEQUENCE: 33

Asp Asp Asp Asp Lys
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34
```

```
Leu Val Pro Arg Gly Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Glu Asn Leu Tyr Phe Gln Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Leu Glu Val Leu Phe Gln Gly Pro
1               5
```

COMPOSITIONS AND METHODS FOR IMMUNOAFFINITY PURIFICATION

RELATED FIELD OF INVENTION

The present invention relates to a process for producing protein molecules by recombinant DNA techniques, and more particularly to a process for producing a selected protein by expression of hybrid molecules composed of the selected protein together with an antigenic peptide, purifying the hybrid molecules by an affinity protocol and optionally cleaving the antigenic peptide from the protein molecule.

BACKGROUND

Proteinaceous molecules, such as enzymes, hormones, storage proteins, binding proteins and transport proteins may be produced by recombinant DNA techniques. For instance, DNA fragments coding for a selected protein, together with appropriate DNA sequences for a promoter and ribosome binding site are ligated to a plasmid vector. The plasmid is inserted within a host prokaryotic or eukaryotic cell. Transformed host cells are identified, isolated and then cultivated to cause expression of the proteinaceous molecules.

The desired protein is then isolated from the culture medium and purified by a variety of techniques employed either individually or in combination. These purification procedures may include techniques to segregate the desired protein based on its molecular size. Such procedures include dialysis, density-gradient centrifugation and gel column chromatography. Dialysis and density-gradient centrifugation, however, are not selective enough to highly purify protein. While the use of gel column chromatography results in greater purification, many of the desired protein molecules are lost during the purification process, thereby resulting in a low yield.

Protein molecules also may be separated from mixture by procedures based on solubility differences. For instance, isoelectric precipitation takes advantage of the change in solubility of proteins as a function of pH while solvent fractionation employs the fact that the solubility of proteins vary as a function of the dielectric constant of the medium. Neutral salts, such as ammonium sulfate, are used to precipitate out proteins as a result of decreased protein solubility based on the high ionic strength of the salt. A severe drawback of solvent fractionation is that solvents can cause the proteins to denature. Neither isoelectric precipitation nor salt precipitation are able to purify proteins beyond a moderate level. One advantage of salt precipitation, however, is that it typically gives close to a 100% yield, and thus this method is often employed as an initial step in tandem with other procedures.

Proteins also may be separated based on their ionic properties, for instance, by various types of electrophoresis or by ion-exchange chromatography. Most electrophoresis techniques are used as analytical tools and are not practical on a large scale basis. While ion-exchange chromatography can result in highly purified proteins, the yield level is typically very low, with many of the protein molecules either being lost in prior eluates or remaining bound to the column matrix.

Affinity chromatography often is employed to avoid the negative aspects of the above-mentioned purification procedures including ion-exchange chromatography and gel column chromatography. Affinity chromatography is based on the capacity of proteins to bind specifically and noncovalently with a ligand. Used alone, it can isolate proteins from very complex mixtures with not only a greater degree of purification than possible by sequential ion-exchange and gel column chromatography, but also without significant loss of activity. See Rosenberry et al., "Purification of Acetylcholinesterase by Affinity Chromatography and Determination of Active Site Stoichiometry," 247 Journal of Biological Chemistry, 1555-1565 (1972). Although affinity chromatography can produce a high level of protein purification, this technique requires the availability of significant amounts of the corresponding ligand (for instance, antibody for antigen or substrate for enzyme) for the protein molecule being isolated. Thus, it may be necessary to carry out a time-consuming, laborious regime of inoculating mice or other animals with the protein molecule of interest in purified form and then identifying a specific ligand for the protein molecule. Thereafter, the ligand must be amplified, for instance, by hybridoma techniques and then purified for covalent detachment to the affinity column matrix.

It will be appreciated that it may be very difficult to isolate a specific ligand for certain protein molecules. Moreover, specific ligands do not exist for all types of protein molecules, such as certain enzymes. As a consequence, to date, affinity chromatography has not been employed as a universal isolation and purification technique for all protein molecules.

SUMMARY OF THE INVENTION

In accordance with the present invention, a hybrid polypeptide composed of a protein of interest and an epitope peptide are produced by recombinant DNA techniques. A preferred epitope sequence comprises the p53 epitope sequence. In one embodiment, the epitope peptide comprises two primary components: a portion reactive with an antibody (i.e., N-terminal, C-terminal or intermediate regions of said polypeptide); and, optionally, a linking portion to connect the epitope peptide to the protein of interest. The linking portion of the epitope peptide, if present, is characterized by being cleavable. Such cleavage may be a result of sequence-specific proteases, photolysis or chemical agents. By this particular construction of the epitope peptide, the hybrid epitope peptide/protein molecules expressed by the transformed host cells can be isolated by affinity chromatography techniques. This is accomplished by constructing an affinity column with immobilized antibodies specific to the antigenic portion of the epitope peptide thereby to bind the expressed hybrid epitope peptide/protein molecule. The bound epitope peptide/protein molecules can be liberated from the column and then the epitope peptide (if desired) is cleaved from the protein molecule thus releasing the desired, highly purified protein molecule.

Accordingly, it is a principle object of the present invention to use recombinant DNA techniques for economically producing a protein of interest and then efficiently purifying the protein.

It is a specific object of the present invention to provide an affinity purification process wherein a single antibody may be employed to isolate and purify substantially all proteins of interest expressed by transformed host cells, whether antigenic or not.

A further particular object of the present invention is to provide a standard, highly efficient process that can be used on a small research level or a large commercial scale to purify substantially all protein molecules produced by recombinant DNA techniques.

An additional particular object of the present invention is to provide a technique that is capable of highly purifying substantially any protein molecule generated by recombinant DNA techniques in a single, affinity chromatography step, but without sacrificing high yields.

Ideally, the amino acid sequence of the optional linking portion is unique, thus minimizing the possibility that an unintended proteolytic agent will inappropriately cleave the protein molecule. In accordance with the present invention, the protein of interest may be composed of any proteinaceous substance that can be expressed in transformed host cells.

One aspect of the present invention contemplates a composition, comprising: a) a first nucleic acid sequence encoding for a protein of interest or portion thereof; and b) a second nucleic acid sequence encoding a p53 epitope, wherein said first nucleic acid sequence is ligated to said second nucleic acid sequence. In one embodiment, the compostion further comprises a third nucleic acid sequence encoding a cleavable linker. In one embodiment, said cleavable linker, upon expression (e.g., in a vector in a host cell) of said third nucleic acid sequence, is attached to the N-terminal end of said protein of interest. It is not intended that the present invention be limited to the order or orientation of how the three sequences are linked. In another embodiment, said cleavable linker, upon expression (e.g., in a vector in a host cell) of said third nucleic acid sequence, is attached to the C-terminal end of said protein of interest. In one embodiment, said epitope sequence, upon expression of said second nucleic acid sequence, is attached to the N-terminal end of said protein of interest. In another embodiment, said epitope sequence, upon expression (e.g., in a vector in a host cell) of said second nucleic acid sequence, is attached to the C-terminal end of said protein of interest. In one embodiment, said encoded p53 epitope is between eight and fifteen amino acids in length. In another embodiment, said encoded p53 epitope comprises an amino acid sequence selected from the group consisting of SEQ ID NOS: 1-18. In one embodiment said composition comprises a vector.

Another aspect of the present invention contemplates a vector comprising: a) a first nucleic acid sequence encoding for a protein of interest or portion thereof; and b) a second nucleic acid sequence encoding a p53 epitope, wherein said first nucleic acid sequence is ligated to said second nucleic acid sequence.

Another aspect of the present invention contemplates a host cell comprising: a) a vector comprising: a) a first nucleic acid sequence encoding for a protein of interest or portion thereof; and b) a second nucleic acid sequence encoding a p53 epitope, wherein said first nucleic acid sequence is ligated to said second nucleic acid sequence. In one embodiment, the host cell is $E.\ coli$. In another embodiment, said host cell is a mammalian cell. In still another embodiment, the host cell is a plant cell. In yet another embodiment, the host cell is yeast or an insect cell.

Another aspect of the present invention contemplates a composition, comprising two contiguous nucleic acid sequences: a) a first nucleic acid sequence encoding for a protein of interest or portion thereof; and b) a second nucleic acid sequence encoding a p53 epitope, wherein said first nucleic acid sequence is ligated to said second nucleic acid sequence. In one embodiment, said encoded p53 epitope is between eight and fifteen amino acids in length. In another embodiment, said encoded p53 epitope comprises an amino acid sequence selected from the group consisting of SEQ ID NOS: 1-18.

Another aspect of the present invention contemplates a vector comprising: two contiguous nucleic acid sequences: a) a first nucleic acid sequence encoding for a protein of interest or portion thereof; and b) a second nucleic acid sequence encoding a p53 epitope, wherein said first nucleic acid sequence is ligated to said second nucleic acid sequence.

Another aspect of the present invention contemplates a host cell comprising: a vector comprising two contiguous nucleic acid sequences: a) a first nucleic acid sequence encoding for a protein of interest or portion thereof; and b) a second nucleic acid sequence encoding a p53 epitope, wherein said first nucleic acid sequence is ligated to said second nucleic acid sequence.

Another aspect of the present invention contemplates a hybrid polypeptide comprising a protein of interest, or portion thereof, linked to a p53 epitope. In one embodiment said p53 epitope comprises an amino acid sequence selected from the group consisting of SEQ ID NOS: 1-18. In one embodiment, said hybrid polypeptide is bound to an antibody. In another embodiment, said hybrid polypeptide is immobilized.

Another aspect of the present invention contemplates a recombinant cloning vector composed of segments of chemically synthesized DNA coding for the epitope peptide. The vector also includes a DNA segment coding for the protein of interest molecule. These DNA segments are inserted within a cloning vector, such as a plasmid, by use of appropriate restriction endonucleases and ligases. Ideally, the plasmid has a phenotypic marker gene for identification and isolation of transformed host cells. In addition, the chosen plasmid preferably includes a natural or synthetic promoter for high level expression of the hybrid epitope peptide/protein molecule in the host cells. The recombinant plasmid is employed to transform compatible prokaryotic or eukaryotic host cells for replication of the plasmid and expression of the hybrid epitope peptide/protein molecule.

The present invention also contemplates the production of an antibody against the antigenic portion of the epitope peptide for affinity column purification of the selected protein molecule. ligand antibodys are generated by immunizing mice, rabbits or other appropriate animals with the epitope peptide that has been chemically synthesized by well-known techniques. To facilitate antibody production, the synthesized epitope peptide can be chemically coupled to a proteinaceous carrier, such as keyhole limpet hemocyanin, bovine or ovine serum albumin or sheep erythrocytes. The substantially larger carrier molecules or cells facilitate recognition of the foreign epitope peptide by the immune system of the inoculated animals.

Another aspect of the present invention contemplates raising antibodies or using commercially available antibodies (see below) with specificity for a portion of the p53 protein. These purified antibodies are subsequently bound to an affinity chromatography column to form an immobilized antibody to capture the hybrid epitope peptide/protein molecules. The hybrid molecules together with growth medium, cell residue, other proteins, etc., are passed over the column, thus binding only the epitope peptide/protein molecules. These bound hybrid molecules are subsquently eluted from the column by chemical means or by competition with soluble epitope peptides. The epitope peptide is then (optionally) cleaved from the protein molecule with a proteolytic agent that is specific to the amino acid sequence of the linking portion of the epitope peptide, chemical agent or by photolysis. Then, the protein of interest is separated from the epitope peptide to release the protein of interest in highly purified form.

It will be appreciated that by virtue of the present invention, only a singular antibody is needed to purify all protein molecules produced by recombinant DNA methods. In addition, the present invention can be used to highly purify all protein molecules produced by recombinant DNA methods, including those that are not susceptible to affinity chromatography procedures.

It is to be understood that some protein products will possess the desired enzymatic or biological activity with the epitope peptide still attached thereto. Such epitope peptide/protein molecules will be useful in such configuration so that their purification will be complete after elution from the antibody column, without need for the proteolytic cleavage step or subsequent steps.

BRIEF DESCRIPTION OF THE DRAWINGS

The details of typical embodiments of the present invention will be described in connection with accompanying drawings, in which:

FIG. 1 displays the amino acid sequence for the full-length wild-type cellular tumor antigen p53 (Accession No.: DNHU53) (SEQ ID NO: 20)

FIG. 2 displays the nucleic acid sequence of the human phosphoprotein p53 gene exon 11 encoding the full length wild-type cellular tumor antigen p53 (Accession No.: M13121 N00032) (SEQ ID NO: 21).

DEFINITIONS

Figure 3:
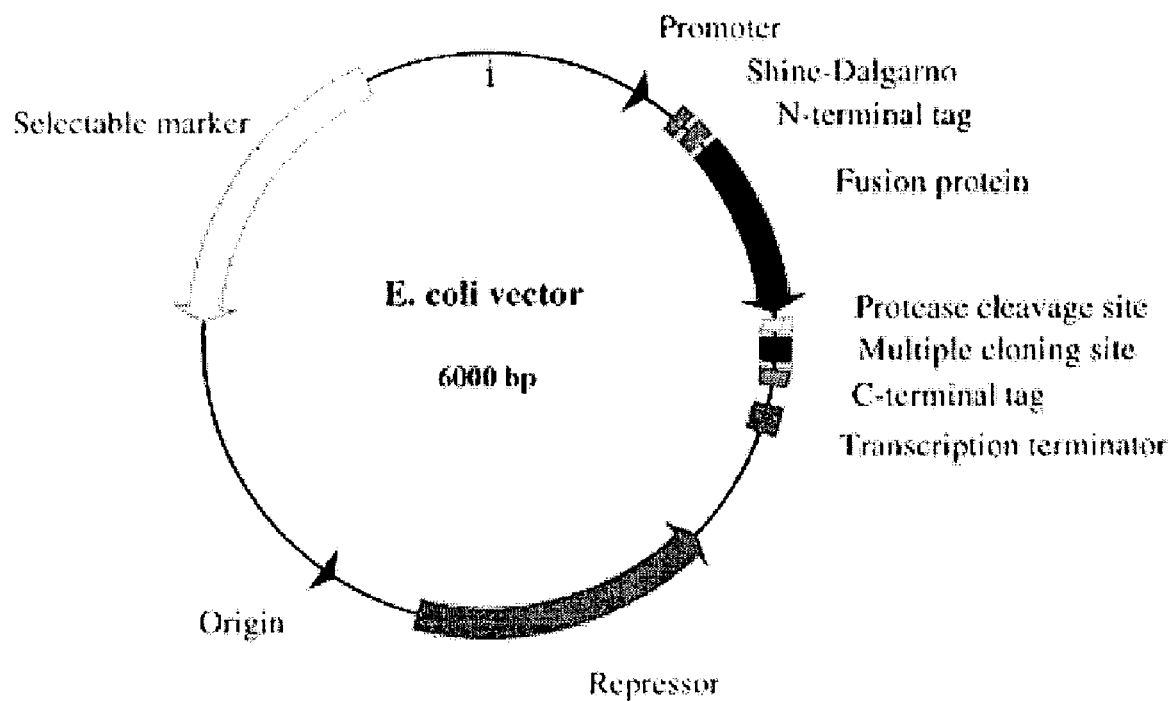
FIG. 3 shows the restriction map of one embodiment for a p53 vector.

The term "protein of interest", as used herein refers to any amino acid based molecule or structure. Specific examples of "protein of interest" include, but are not limited to, catalytic peptides (e.g., catalytic oligopeptides); metabolic proteins (e.g., energy creation proteins, hemoglobin, myoglobin, proteases, ATPases, polymerases, recombinases, synthetases, isomerases, esterases, dehydrogenases, hyrdrolases, nucleases, topoisomerases, kinases, phosphatases, reductases, oxidases, ligases, lysozymes, energy degradation proteins, cell synthesis proteins, cytochrome P450s); structural proteins (e.g., collagen, histones, actin, myosin, membrane proteins, tubulin, integrin); motor proteins (e.g., actin, myosin); antibodies (e.g., Immunoglobulins); signaling proteins (e.g., G-proteins, actin, signal peptidases).

The term "iportion" may refer to a relatively small segment of a protein or a small segment of an oligonucleotide. In a preferred embodiment, a portion of a protein refers to a range of between 5-100 contiguous amino acids while a portion of a nucleic acid refers to a range of between 15-300 contiguous nucleic acids.

The term "sequence corresponding to a promoter" refers to a non-coding nucleic acid region that is responsible for the regulation of transcription (an open reading frame) of the DNA coding for the protein of interest.

The term "sequence corresponding to a ribosome binding site" refers to a coding nucleic acid region that, when transcribed, allows the binding a mRNA in such a manner that translation occurs.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term, "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably more than three, and usually more than ten and can be 300 or more. The exact size will depend on many factors, which in turn depends on the ultimate function or use of the oligonucleotide. The oligonucleotide may be generated in any manner, including chemical synthesis, DNA replication, reverse transcription, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used hererein, a nucleic acid sequence, even if internal to a larger oligonucleotide, also may be the to have 5' and 3' ends. When two different, non-overlapping "oligonucleotides" anneal to different regions of the same linear complementary nucleic acid sequence, and the 3' end of one oligonucleotide points towards the 5' end of the other, the former may be called the "upstream" oligonucleotide and the latter the "downstream" oligonucleotide. The present invention contemplates the situation where the epitope is upstream or downstream of the protein of interest.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or may be produced synthetically. A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "hybridize" and "hybridization", as used herein refer to the annealing of a complementary sequence to the target nucleic acid (the sequence to be detected) through base pairing interaction. Marmur et al., Proc. Natl. Acad. Sci. USA 46:453 (1960) and Doty et al., Proc. Natl. Acad. Sci. USA 46:461 (1960).

The terms "annealed" and "hybridized", as used herein, are interchangeable throughout, and are intended to encompass any specific and reproducible interaction between an oligonucleotide and a target nucleic acid, including binding of regions having only partial complementarity and binding interactions that make use of non-canonical interactions for stability and/or specificity.

The term "complement", of a nucleic acid sequence, as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "probe", as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

The term "label", as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The term "substantially single-stranded" when used in reference to a nucleic acid means that the nucleic acid exists primarily as a single strand of nucleic acid in contrast to a double-stranded nucleic acid which exists as two strands of nucleic acid which are held together by inter-strand base pairing interactions.

The term "nucleic acid", as used herein refers to single or double strands of DNA or RNA that may have the same, or different sequences.

The term "variant", as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene vary in sequence from one another. A second mutant form of the structural gene may exist. This second mutant form varies in sequence from both the wild-type gene and the first mutant form of the gene.

The phrase "oligonucleotide primers matching or complementary to a gene sequence", as used herein refers to oligonucleotide primers capable of facilitating the template-dependent synthesis of single or double-stranded nucleic acids. Oligonucleotide primers matching or complementary to a gene sequence may be used in PCRs, RT-PCRs and the like. An oligonucleotide primer need not be perfectly complementary to a target or template sequence. A primer need only have a sufficient interaction with the template that it can be extended by template-dependent synthesis.

The term "cleavable linker" as used herein, refers to an amino acid sequence which is linked to an epitope tag or a protein of interest, the resulting structure being cleavable by means selected from, but not limited to, the group consisting of chemicals, light, proteases, and enzymes. A cleavable linker is linked to the epitope tag or protein of interest at either the N-terminal or C-terminal end of said epitope tag or protein of interest.

The term "microorganism", as used herein means an organism too small to be observed with the unaided eye and includes, but is not limited to bacteria, virus, protozoans, fungi, and ciliates.

The term "microbial gene sequences", as used herein refers to gene sequences derived from a microorganism.

The term "bacteria", as used herein refers to any bacterial species including eubacterial and archaebacterial species. Bacterial expression systems and host cells are contemplated. *E. coli* is a preferred host cell.

The term "virus", as used herein refers to obligate, ultra-microscopic, intracellular parasites incapable of autonomous replication (i.e., replication requires the use of the host cell's machinery).

The term "non-contiguous," as used herein is intended to mean that the regions are separated by intervening nucleic acid (or non-nucleic acid spacers). It is not intended that the present invention be limited by the size of the intervening nucleic acid (or the size of non-nucleic acid spacers).

As used herein, the term "poly-histidine tract" or (HIS-tag) refers to the presence of two to ten histidine residues at either the amino- or carboxy-terminus of a nascent protein A poly-histidine tract of six to ten residues is preferred. The poly-histidine tract is also defined functionally as being a number of consecutive histidine residues added to the protein of interest which allows the affinity purification of the resulting protein on a nickel-chelate column, or the identification of a protein terminus through the interaction with another molecule (e.g. an antibody reactive with the HIS-tag).

The term "epitope", as used herein refers to any amino acid sequence having antigenic properties. An epitope is capable of stimulating the production of antibodies, with or without a hapten, and is capable of binding antibodies having specificity for the epitope.

The term "p53-derived epitope", as used herein refers to any amino acid sequence comprising the wild type sequence (i.e., SEQ ID NO: 1) or variant.

The term "p53 variant", as used herein refers to any amino acid sequence that differs from the wild type sequence (i.e., SEQ ID NO: 1) in at least one, but not more than three residues.

The term "vector" as used herein refers to any oligonucleotide encoding a protein of interest that is capable of transforming a host cell under conditions that a protein of interest is expressed.

The term "host cell" as used herein refers to any organism, eukaryotic or prokaryotic, that is capable of transformation by a vector comprising a protein of interest. The host cell may be, but not limited to, a virus, bacteria, yeast, insect, plant or mammal cell. Preferable, such host cells are *E. coli* cells.

The term "hybrid polypeptide" as used herein refers to any polypeptide that is generated by the peptide linkage of at least two proteins or at least two portion of proteins. Such hybrid polypeptides are synonomous with fusion proteins.

DETAILED DESCRIPTION

In accordance with the present invention, hybrid polypeptide molecules comprising an epitope peptide and proteins of interest are produced by recombinant DNA techniques and then the hybrid molecules are purified by an affinity chromatography process utilizing an epitope specific antibody. In a preferred embodiment, a DNA expression vector is formed that includes segments of DNA coding for the epitope peptide and the protein of interest. In one embodiment, the linking portion of the epitope peptide is a cleavable linker having specific amino acid residues adjacent the selected protein molecule that allow digestion by proteolytic enzymes or chemical proteolytic agents. In another embodiment, the linking portion of the epitope is not cleaved. Subsequent to cleavage of the linker portion, the cloning vector is replicated and the hybrid polypeptide is expressed in prokaryotic or eukaryotic cells transformed by the vector. The transformed cells are isolated and then expanded, for instance, in culture or by fermentation process.

Thereafter, the expressed hybrid polypeptide is purified by affinity chromatography. Antibodies specific to the antigenic portion of the epitope peptide are generated or purchased (i.e., for example from Santa Cruz Biotechnology, Santa Cruz, Calif.) for attachment to a bead column or other type of suitable matrix. An extract of the host cells made from the culture or fermentation is applied to the column and then the polypeptides that bind to the column are eluted. Thereafter, the epitope peptide is optionally cleaved from the peptide molecule with an appropriate proteolytic enzyme or chemical agent, thereby releasing the desired mature protein molecule in a highly purified, highly active state.

Epitope Peptide

The epitope peptide of the present invention is in the form of a linear sequence of amino acids bonded to the N-terminus, C-terminus or within the sequence of the protein of interest. In one embodiment, this linear sequence is composed of two basic portions: an "antigenic portion" and a "linking portion" to link the epitope peptide to the selected protein of interest. As noted above, and as more fully discussed below, the antigenic portion of the epitope peptide serves to facilitate isolation and purification of the hybrid polypeptide produced by the transformed host cells. The antigenic portion binds to a specific antibody (i.e., for example, a p53 antibody) which has been immobilized on a chromatography column or other matrix.

The present invention contemplates a p53 epitope, whether a portion of the wild type sequence or a variant thereof. In one embodiment, the present invention contemplates the wild type amino acid sequence: T F S D L W K L L (SEQ ID NO:1) as well as the nucleic acid sequence coding for this sequence. In one embodiment, the present invention contemplates the wild type amino acid sequence: T F S D L W K L (SEQ ID NO:2) as well as the nucleic acid sequence coding for this sequence. In one embodiment, the present invention contemplates the wild type amino acid sequence: F S D L W K L L (SEQ ID NO:3) as well as the nucleic acid sequence coding for this sequence. In another embodiment, the present invention contemplates variants of the general formula: T F S D L [x] K L L, wherein [x] can be any amino acid other than W (SEQ ID NO:25). Examples of such variants include (but are not limited to):

```
        T F S D L H K L L        (SEQ ID NO:4)

T F S D L Y K L L        (SEQ ID NO:5)

T F S D L G K L L        (SEQ ID NO:6)

T F S D L N K L L        (SEQ ID NO:7)

T F S D L F K L L        (SEQ ID NO:8)

T F S D L D K L L        (SEQ ID NO:9)

T F S D L T K L L        (SEQ ID NO:10)
```

In another embodiment, the present invention contemplates variants of the general formula:

[z]$_y$ T F S D L [x] K L L, wherein [x] can be any amino acid other than W, [z] can be any amino acid including but not limited to the amino acids corresponding to the wild-type sequence, and y is an integer between 1 and 10.

Examples of such variants include (but are not limited to):

```
    E T F S D L H K L L          (SEQ ID NO:11)

Q E T F S D L H K L L        (SEQ ID NO:12)

S Q E T F S D L H K L L      (SEQ ID NO:13)

L S Q E T F S D L H K L L    (SEQ ID NO:14)
```

In another embodiment, the present invention contemplates variants of the general formula:

[z]$_y$ T F S D L [x] K L L [z]$_y$, wherein [x] can be any amino acid other than W, [z] can be any amino acid including but not limited to the amino acids corresponding to the wild-type sequence, and y is an integer between 1 and 10 (SEQ ID NO:26).

Examples of such variants include (but are not limited to):

```
    E T F S D L H K L L P        (SEQ ID NO:15)

Q E T F S D L H K L L P      (SEQ ID NO:16)

S Q E T F S D L H K L L P    (SEQ ID NO:17)

L S Q E T F S D L H K L L P E (SEQ ID NO:18)
```

In one specific exemplary embodiment, a nucleic acid sequence of a p53 epitope comprises the sequence: CAG-CAGCTTGTGCAGGTCGCTGAAGGT (SEQ ID NO: 22).

Cleavable Linker

In accordance with one embodiment of the present invention, the linking portion of the epitope peptide serves to connect the epitope peptide to the protein of interest. However, once the hybrid polypeptide, composed of the epitope peptide and the protein of interest, has been purified from the culture extract, the epitope peptide is preferably cleaved from the protein of interest. Thus, in one embodiment, the linking portion of the epitope peptide is cleavable at a specific amino acid residue, and ideally at the residue adjacent the N-terminus of the protein molecule. As such, the linking portion is composed of preferably four to six amino acids that are cleavable at a desired residue by a sequence specific proteolytic enzyme or chemical proteolytic agent. However, it is to be understood that the number of residues composing the linking portion may vary from this ideal number without departing from the scope of the present invention.

The present invention contemplates proteolytic cleavage of an epitope tag coupled to a protein of interest and/or a linker. Epitope tagged recombinant proteins have become a valuable tool in studying protein structure and function. The small size and low immunogenicity of the epitope tag means that its removal is not usually required. However, there are some applications, such as structure-determination studies by X-ray or NMR, or the production of therapeutics, where a protein product free from vector-derived amino acids may be preferred.

In one embodiment, the proteolytic cleavage is achieved by the TAGZyme System (Quiagen) utilizing recombinant exoprotease. The action of this exoprotease allows a highly efficient (i.e., approximately 95% digestion in 30 min at 37° C.)

and precise removal of N-terminal His tags from proteins. This enzyme has a highly specific exoproteolytic digest meaning that no nonspecific cleavage occurs within the body of the protein.

In another embodiment, the DAPase Enzyme is contemplated to sequentially cleave off dipeptides from the N-terminus of a purified tagged protein. Digestion is halted when the enzyme reaches a "stop point", which is an amino acid motif that cannot serve as a substrate. Table 1 provides Natural DAPase stop points (↓). These stop points have the characteristics that dipeptide degradation (underlined) will cease when encountering a Lys, Arg, Gln († In the presence of excess Qcyclase Enzyme thus converings the glutamine residue to pyroglutamate) or when a Pro is either one or two residues from the stop point.

TABLE 1

DAPase Stop Points

| Amino Acid | DAPase Stop Point (↓) Sequence |
|---|---|
| Lysine (Lys, K) | Xaa-Xaa . . . Xaa-Xaa ↓ Lys-Xaa . . . (SEQ ID NO:27) |
| Arginine (Arg, R) | Xaa-Xaa . . . Xaa-Xaa ↓ Arg-Xaa . . . (SEQ ID NO:28) |
| Glutamine (Gln, Q)† | Xaa-Xaa . . . Xaa-Xaa ↓ Gln-Xaa . . . (SEQ ID NO:29) |
| Proline (Pro, P) | Xaa-Xaa . . . Xaa-Xaa ↓ Xaa-Pro-Xaa-Xaa . . . (SEQ ID NO:30) |
| Proline (Pro, P) | Xaa-Xaa . . . Xaa-Xaa ↓ Xaa-Xaa-Pro-Xaa . . . (SEQ ID NO:31) |

A DAPase stop point can be introduced into a protein sequence by inserting a glutamine codon into the expression construct. The glutamine residue is introduced at an odd-numbered position directly behind the epitope tag and directly before the first amino acid of the native protein.

In another embodiment, recognition sequence cleavage sites can be incorporated into recombinant proteins. For an N-terminal epitope tag, the cleavage site may be incorporated immediately after the epitope tag and before the first amino acid of recombinant protein. Alternatively, for a C-terminal epitope tag, the cleavage site may be incorporated between the last amino acid of recombinant protein and the first amino acid of epitope tag. Table 2 represents some of the commonly used proteases and their cleavage sites.

TABLE 2

Protease cleavage sites

| Protease | Recognition Sequence |
|---|---|
| Factor Xa | Ile Glu/Asp Gly Arg ¦ (SEQ ID NO:32) |
| Enterokinase | Asp Asp Asp Asp Lys ¦ (SEQ ID NO:33) |
| Thrombin | Leu Val Pro Arg ¦ Gly Ser (SEQ ID NO:34) |
| TEV protease | Glu Asn Leu Tyr Phe Gln ¦ Gly (SEQ ID NO:35) |
| PreScission | Leu Glu Val Leu Phe Gln ¦ Gly Pro (SEQ ID NO:36) |

For a chosen composition of the epitope peptide, DNA oligomers coding for the amino acids of the epitope peptide may be synthesized using commercially available, automated DNA synthesizer in a manner well known in the art. Because the techniques and apparatus for synthesizing DNA are now common in the art, they need not be set forth here. As discussed below, the synthetic DNA oligomers may be ligated to a DNA sequence coding for the protein of interest and then the combined DNA fragments ligated to an appropriate expression vector to form a cloning vehicle for transformation to an appropriate host cell.

Protein of Interest

The present invention may be beneficially employed to produce substantially any prokaryotic or eukaryotic, simple or conjugated, protein of interest that can be expressed by a vector in a transformed host cell. Such proteins of interest include, but are not limited to, enzymes, whether oxidoreductases, transferases, hydrolases, lyases, isomerases or ligases.

The present invention also contemplates the production of storage proteins, such as ferritin or ovalbumin or transport proteins, such as hemoglobin, serum albumin or ceruloplasmin. Also included are the types of proteins that function in contractile and motile systems, for instance, actin and myosin.

The present invention also contemplates the production of proteins that serve a protective or defense function, such as the blood proteins thrombin and fibrinogen. Other protective proteins include the binding proteins, such as antibodies or immunoglobulins that bind to and thus neutralize antigens.

The protein produced by the present invention also may encompass various hormones such as human growth hormone, somatostatin, prolactin, estrone, progesterone, melanocyte, thryotropin, calcitonin, gonadotropin and insulin. Other such hormones include those that have been identified as being involved in the immune system, such as interleukin 1, interleukin 2, colony stimulating factor, macrophage-activating factor and interferon.

Proteins that serve as structural elements may be produced by the present invention; such proteins include the fibrous proteins collagen, elastin and alpha-keratin. Other structural proteins include glyco-proteins, virus-proteins and muco-proteins.

In addition to the above-noted naturally occurring proteins, the present invention may be employed to produce synthetic proteins defined generally as any sequence of amino acids not occurring in nature.

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthesized plasmids having genes coding for many different protein molecules are now commercially available from a variety of sources. The desired DNA also can be produced from mRNA by using the enzyme reverse transcriptase. This enzyme permits the synthesis of DNA from an RNA template.

Preparation of DNA Expression Vectors

In accordance with the present invention, once a gene coding for a protein of interest molecule is isolated, synthesized or otherwise obtained, it is joined to a synthetic DNA fragment coding for the epitope peptide. As noted above, the epitope peptide gene may be synthesized by well-known techniques which will not be repeated here. In addition to the protein of interest gene and the epitope peptide gene, if needed, the hybrid DNA fragment may include a ribosome binding site for high level protein translation in a host cell, a translation initiation codon (ATG), and a promoter.

In general, the genes coding for the protein of interest and the epitope peptide ideally are treated with an appropriate restriction enzyme or are otherwise manipulated to have cohesive termini to facilitate ligation with each other and with a plasmid or other type of cloning vector. The cloning vector is preferably digested with the same restriction endonuclease used to condition the foreign genes to form complementary cohesive termini prior to ligation with the foreign genes. The resulting cloning vector is used to transform a host microorganism. The transformants are isolated and analyzed for the presence of the foreign genes and for the proper orientation of the genes within the vector. The transformants are then multiplied in culture to cause replication of the vector and high level expression of the hybrid polypeptide being sought. In addition, the cloning vectors may be used to transform other strains of the chosen host or other types of hosts for large scale production of the hybrid heterologous polypeptide. Various procedures and materials for preparing recombinant vectors, transforming host cells with the vectors, replicating the vector and expressing polypeptides and proteins are discussed by Old and Primrose, Principals of Gene Manipulation, (2d Ed. 1981), which disclosure is incorporated herein by reference.

To carry out the present invention, various cloning vectors may be utilized. Although the preference is for a plasmid, the vector may be a bacteriophage or cosmid. If cloning takes place in mammalian or plant cells, viruses can be used as vectors. If a plasmid is employed, it may be obtained from a natural source or artificially synthesized. The particular plasmid chosen should be compatible with the particular cells serving as the host, whether a bacteria such as *Escherichia coli* (*E. coli*), yeast, or other unicellular microorganism.

The size of the plasmid must be sufficient to accommodate the hybrid genes coding for both the protein molecule of interest and the epitope peptide, but also of as low a molecular weight as possible. Low molecular weight plasmids are more resistant to damage from shearing and are more readily isolated from host cells. If obtained from natural sources, they are usually present as multiple copies, thereby facilitating their isolation. Also, there is less likelihood that a low molecular weight plasmid has multiple substrate sites for restriction endonucleases.

A plasmid cloning vector may also have restriction enzymes to cleave the plasmid for subsequent ligation with the foreign genes without causing inactivation of the replicon while providing suitable ligatable termini that are complementary to the termini of the foreign genes being inserted. To this end, it would be helpful for the plasmid to have single substrate sites for a large number of restriction endonucleases.

Moreover, the plasmid should have a phenotypic property that will enable the transformed host cells to be readily identified and separated from cells which do not undergo transformation. Such phenotypic selection genes can include genes providing resistance to a growth inhibiting substance, such as an antibiotic. Plasmids are now widely available that include genes resistant to various antibiotics, such as tetracycline, streptomycin, sulfa drugs, penicillin, and ampicillin. When host cells are grown in a medium containing one of these antibiotics, only transformants having the appropriate antibiotic resistant gene will survive.

Rather than utilizing a gene resistant to a growth inhibiting compound to identify transformed host cells, phenotypic selection genes can also include those that provide growth factor to permit transformed cells to propagate in a medium which lacks the necessary growth factor for the host cells. For instance, for yeast auxotrophs, such growth factors include tryptophan or leucine.

In one embodiment, the present invention contemplates the construction of a vector comprising nucleic acid sequences for an epitope tag, a cleavage linker and a protein of interest. In one embodiment, an *E. coli* expression vector is contemplated (See FIG. 3).

The presence of a selectable marker within the vector is useful since in the absence of selective pressure plasmids are lost from the host. This problem is even more prevalent in the presence of a very high copy number of plasmids and when plasmid-borne genes are toxic to the host or otherwise significantly reduce its growth rate. For example, the same plasmid may contain an antibiotic-resistance marker so supplementation of the medium with the appropriate antibiotic will kill only plasmid-free cells, thereby allowing plasmid-containing cells to proliferate.

An efficient vector requires a promotor to initiate transcription. Promoters may be positioned approximately between 10-100 nucleotides upstream of the ribosome binding site. While many promoters are contemplated by this invention a preferred promoter exhibits several desirable features: i) it is strong enough to allow product accumulation up to 50% of the total cellular protein;, ii) it has a low basal expression level (i.e. it is tightly regulated to prevent product toxicity) and iii) it is easily inducible. One specific problem known to those skilled in the art is that many promoters "leak" expression protein (i.e., gene product is expressed at low level before the addition of the inducer). This problem may become acute if the gene product is toxic to the host. This invention, in one embodiment, contemplates preventing "promotor leakage" by the incorporation of regulatory gene that produces a repressor protein. For example, lac-derived promoters are regulated by the insertion of a lac-operator sequence downstream of the promoter sequence. The lac-promoters are known to control the expression of the lac-repressor by host strains carrying the lacI$^q$ allele (for expressing a medium copy number of plasmids) or from the same or a helper plasmid (for higher copy number plasmids). Alternatively, repression can be achieved by the addition of 1% glucose to the culture medium.

The plasmid construction is also important to manipulate the resulting level of protein expression. For example, a complete vector also is contemplated to contain: i) an origin of replication to control the plasmid copy number; ii) a start codon that is the initiation point of translation. In one embodiment the start codon is selected from the group consisting of ATG, GTG, TTG and TAA; iii) a transcription terminator to reduce unwanted transcription and increase plasmid and mRNA stability, and iv) a Shine-Dalgarno (SD) sequence (i.e., complementary to the 3'-end of the 16S ribosomal RNA) to provide initial ribosomal contact and binding necessary to initiate the translation process. The efficiency of translation initiation at the start codon depends on the actual SD sequence; the present invention contemplates using an SD concensus sequence comprising 5'-TAAGGAGG-3' (SEQ ID NO.:19). The SD sequence is contemplated to be positioned approximately between 4-14 nucleotides upstream the start codon with the optimal spacing of being about 8 nucleotides. In one embodiment, the SD sequence contains a plurality of adenosine nucleotides. While it is not necessary to understand the underlying mechanisms of an invention, it is believed that an SD sequence rich in adensosine nucleotides have reduced formation of secondary structures thus avoiding a consequential reduction in protein expression levels.

If *E. coli* is employed as the host cell, a preferred plasmid for performing the present invention is pYEJ001 (PL Biochemicals). This plasmid has genes coding for both ampicillin and tetracycline resistance. It also includes an origin of replication for propagation in *E. coli* and has both a lac operon and synthetic promoter sites for high level expression of foreign genes in *E. coli*.

An alternative plasmid for high level expression in *E. coli* is pBR322. This plasmid was constructed and described by Bolivar et al., 2 Gene 95-113 (1977) and has been highly characterized and fully sequenced by Sutcliffe, 43 Cold Spring Harb. Symp. Quant. Biol., (1) 77-90 (1979).

If yeast cells are employed as transformants, p219 is a preferable plasmid. Samples of this plasmid are on deposit with the American Type Culture Collection (ATCC), 12361 Parklawn Drive, Rockville, Md. 20852, under accession number 39550. This plasmid has a yeast promoter sequence for propagation of the plasmid in both yeast and *E. coli*. In addition, it has a selectable marker, ampicillin resistant gene, for selection of the plasmid in *E. coli* and the yeast trp 1 gene for selection in yeast trp-auxotrophs.

If a bacteriophage is used instead of a plasmid, such phages should have substantially the same characteristics used to select a plasmid as discussed above. This includes the existence of a phenotypic marker gene and ligatable termini for attachment to foreign hybrid genes coding for the epitope peptide and the protein molecule of interest.

To prepare the chosen plasmid for ligation, preferably, it is digested with a restriction endonuclease to produce a linear segment(s) in which the two DNA strands are cleaved at closely adjacent sites to produce cohesive termini ("sticky ends") bearing 5'-phosphate and 3'-hydroxyl groups, thereby facilitating ligation with the foreign genes. For the plasmids identified above, the restriction endonucleases Hind III and Eco RI will produce this result. Other restriction endonucleases may be employed to cleave the plasmids at other target sites. Also, the plasmid may be sequentially treated with two different restriction endonucleases to produce dissimilar termini configurations to facilitate ligation of foreign DNA fragment(s) in the proper orientation.

Certain restriction enzymes (Pvu II, Bal I) may result in the formation of square or blunt ends. The square ends of the plasmid can be joined to the foreign genes with an appropriate ligase. Alternatively, nucleic acids can be added to the 5' and or 3' ends to form cohesive termini, for instance, by use of linker molecules. Instead, bases may be removed from the flush ends with appropriate enzymes to form cohesive termini. The methods and materials for achieving this are well known in the art. See Old and Primrose, supra.

Ideally, the linearized plasmid vector is treated with an alkaline phosphatase to remove the 5'-terninal phosphate groups. This will prevent recircularization of the plasmid; it will leave one nick at each end of the foreign DNA remaining unligated from the plasmid. However, after transformation of a host organism, cellular repair mechanisms will repair the nick.

It is to be appreciated that digestion of the chosen plasmid with a restriction endonuclease(s) may result in the formation of two or more linear DNA segments. The segment to be used to form the cloning vector (i.e., the segment having the phenotypic identity gene, replicon and other desired components) may be identified by well-known techniques, such as by gel electrophoresis.

Prior to being joined with the selected cloning vector, it is desirable, in one embodiment, that the foreign genes coding for the epitope peptide and the selected protein are first joined together. Ideally, the gene coding for the protein molecule is treated with the same restriction endonuclease used to cleave the plasmid vector so that the appropriate terminus of the gene will be compatible with the corresponding terminus of the plasmid. This gene also may be treated with a second, different restriction endonuclease to prepare its opposite terminus for ligation with the epitope peptide gene.

Since the gene coding for the epitope peptide is formed by chemical synthesis, it can be constructed with appropriate termini configurations to facilitate ligation to the protein molecule gene and the corresponding terminus of the plasmid. Oligomers coding for the ribosome binding site and a translation initiation codon (ATG) may also be synthesized. The synthetic DNA oligomers for the epitope peptide, ribosome binding site and translation initiation codon are joined to the protein molecule gene in vitro with an appropriate DNA ligase, by established techniques.

In the ligation reaction, adenosine triphosphate (ATP), nicotinamide-adenine dinucleotide (NAD+) or other appropriate cofactors are used with the DNA ligase. In addition, dithiothreitol may be added as a reducing agent and spermidine added as a DNA stabilizer. Also, a protein source, such as bovine serum albumin (BSA) can be employed to prevent denaturization In one embodiment, the molar ratio of the genes coding for the protein molecule and the synthetic oligomers are in the range of about 1-5:5-1. After ligation the resulting DNA strands are analyzed, for instance, by gel electrophoresis, to identify whether those composed of segments of DNA coding for the protein molecule are properly cointegrated with the synthetic oligomers.

The cointegrate genes are next ligated to the linearized plasmid fragment in a solution containing a ligase buffer and an appropriate DNA ligase. Preferably, the molar ratio of plasmids to the cointegrate genes is in the range of about 1-5:5-1. As in the ligation of the protein molecule gene to the epitope peptide gene, discussed above, this ligation protocol also requires a coenzyme such as ATP or NAD$^+$ and preferably utilizes a protein source, reducing agent and DNA stabilizer. After incubation, the recircularized plasmid having the current orientation of the cointegrate genes are identified by standard techniques, such as by gel electrophoresis.

Transformation with Recombinant DNA Plasmid

The recombinant DNA plasmids, as prepared above, are used for the transformation of host cells. Although the host cell may be any appropriate prokaryotic or eukaryotic cell, preferably it is a well-defined bacteria, such as *E. coli* or a yeast strain. Both such hosts are readily transformed and capable of rapid growth in fermentation cultures. In place of *E. coli*, other unicellular microorganisms can be employed, for instance fungi and algae. In addition, other forms of bacteria such as salmonella or pneumococcus may be substituted for *E. coli*. Whatever host is chosen, it should be one that does not contain a restriction enzyme that would cleave the recombinant plasmid and that has the necessary biochemical pathways for phenotypic expression and other functions for proper expression of the hybrid polypeptide.

If *E. coli* is chosen, preferable strains include RR1 and HB 101, both of which are widely available. For transformation in yeast, preferable strains include DB 746 and DBK 747. These strains also are widely available (for instance, from the ATCC as strain Nos. 44 773 and 44 774, respectively).

The techniques for transforming recombinant plasmids in *E. coli* strains are widely known. A typical protocol is set forth in U.S. Pat. No. 4,332,900, hereby incorporated by reference. Procedures for transforming yeast cells with recombinant plasmids are also known. See Beggs, 275 Nature 104-109 (1978). In transformation protocols, only a small portion of the host cells are actually transformed, due to limited plasmid uptake by the cells. Thus, before transformants are isolated, the host cells used in the transformation protocol typically are multiplied in an appropriate medium. The cells that actually have been transformed can be identified by placing the original culture on agar plates containing a suitable growth medium containing the phenotypic identifier, such as an antibiotic. Only those cells that have the proper resistant gene will survive. Cells from the colonies that survive can be lysed and then the plasmid isolated from the lysate. The plasmid thus isolated can be characterized inter alia to determine if the cointegrate genes are ligated in the correct orientation, by digestion with restriction endonucleases and subsequent gel electrophoresis or by other standard methods.

Once transformed cells are identified, they can be multiplied by established techniques, such as by fermentation. In addition, the recovered cloned recombinant plasmids can be used to transform other strains of bacteria or other types of host cells for high scale replication and expression of the hybrid polypeptide.

Purification of Hybrid Polypeptide

The hybrid polypeptides expressed by the transformed host cells are separated from the culture medium, other cellular material, etc. preferably by an affinity chromatography process. Antibodies against the epitope peptide portion of the hybrid polypeptide are attached onto a column matrix, or other solid support. This bound antibody is contacted with an extract from the transformed host cells and captures the hybrid polypeptide. The hybrid polypeptide is eluted from the column, for instance, by competition from soluble epitope peptide. The hybrid epitope peptide is cleaved from the protein of interest thereby resulting in a purified protein.

Chemical Synthesis of Epitope Peptides

In one embodiment, the epitope peptide may be chemically synthesized. The synthesized epitope peptide includes amino acid residues forming an antigenic N-terminal portion that is bonded to adjacent residues forming a linking portion of the peptide. Alternatively, the antigenic portion may be the C-terminal portion or between the C-terminal and N-terminal regions of the hybrid polypeptide. The particular amino acid residues employed in these two portions of the epitope polypeptide were detailed above.

The synthesis technique employs widely available solid resin particles, for instance beads, that are large enough to be separated from liquid phase by filtration. Such particles are available with an initial amino acid, such as Gly, already attached to them. Moreover, the initial amino acid is typically provided as a N-alpha-butyloxycarbonyl (N-alpha-BOC) derivative, with both its end and side chains protected. This protected initial amino acid is prepared for attachment to a diamino acid by treating the residue with a dilute acid to remove the N-alpha-BOC group. Deprotection is confirmed by conducting a standard ninhydrin test on a small sample of the resin. If the resin has not been deprotected, the above procedure is repeated, however, if the resin has been deprotected, the amino acid is neutralized with a hindered base and then is ready for reaction with a first diamino acid.

The diamino acid may be differentially protected, for instance, in the form of N-alpha-tertiary butyloxycarbonyl-epsilon-fluorenylmethyloxycarbonyl (N-alpha-BOC-FMOC) derivative. This particular derivative allows the selected deprotection of the epsilon amino group for coupling of the diamino acid to a fatty acid or other lipophilic, micelle forming substance. Thereafter, the alpha-BOC group is removed by the usual acid treatment and the next amino acid residue added. To couple the diamino acid to the residue, it is activated with a carbodiimide condensing agent and is mixed with the resin. Thereafter, a ninhydrin test conducted to ascertain whether coupling has taken place.

After the last residue of the antigenic portion of the peptide is coupled to the resin, its N-terminus is deprotected with a dilute acid. Thereafter, side blocking groups of the residues are deprotected and the peptide cleaved from the resin by a standard acid treatment. Lastly, the peptide is isolated from the resin.

The epitope peptide described above can be constructed without the linking portion. Instead, the antigenic epitope residues prepared by the above methods, can be coupled directly to the protein of interest without seriously compromising the ability of the epitope peptide to attach antibodies Although the epitope peptides have been described as being chemically synthesized with a solid phase resin, the synthesis procedure can be performed entirely in solution without the resin. In this case, the reactions and the final products are essentially identical to those described above.

ELISA Assay

As noted above, the polyclonal antibody, hybridoma supernates and monoclonal antibodies were tested for anti-epitope peptide responses in an ELISA assay as described by Engvall et al. in "Enzyme-linked immunosorbent assay (ELISA): quantitative assay for immunoglobulin," 8 Immunochemistry 871-874 (1971). Since this type of assay is well known it will only be briefly outlined here.

Epitope peptide is diluted to a concentration of approximately 1 microgram (ug) per milliliter in phosphate buffered saline (PBS). Approximately 25 microliters (ul) of this solution is placed in replicate microliter plate wells. The fluid from the solution is allowed to evaporate during an incubation process thereby to non-specifically adhere the synthetic peptide to the plastic well walls. After each well is washed with approximately 100 ul of PBS, additional PBS containing 1% (by weight) bovine serum albumin (BSA) is added to each well and then the plate incubated at 37° C. for an additional hour to block all of the remaining sites on the bottom of the plastic well that have not already bound the epitope peptide. The BSA thereby prevents non-specific adherence of the antibody of interest to the wells. After this additional incubation, the PBS solution is decanted.

Next, samples to be tested (i.e., for example, animal serum containing polyclonal antibodies, monoclonal antibodies or hybridoma supernates) are added to the wells and incubated for approximately 90 minutes at 37° C. After incubation, the antibody solutions are removed and each well repeatedly washed with PBS or by rinsing with tap water. Thereafter, approximately 50 ul of an enzyme-labeled anti-immunoglobulin antibody is added to each well, for instance, an alkaline phosphatase conjugated secondary antibody. If the assay is being employed to detect hybridoma sup emates with anti-epitope peptide reactivity, the alkaline phosphatase conjugated reagent is a goat anti-mouse IgG antibody (Sigma Chemical Co., St. Louis, Mo.) used at a 1:700 dilution in PBS containing approximately 1% BSA. If the assay is being employed to detect polyclonal antibodies to the epitope peptide, for instance from rabbit sources, the alkaline phosphatase conjugated reagent is a goat anti-rabbit IgG antibody (Sigma Chemical Co., St. Louis, Mo.) used at approximately 1:200 dilution in PBS containing approximately 1% BSA.

After reactions with the appropriate alkaline phosphatase coupled antibody, each well is repeatedly washed with either normal saline (approximately 0.9% weight/volume) or by immersion in tap water. Next, approximately 100 ul of a colorless alkaline phosphatase substrate is then added to each well. One such substrate is para-nitrophenyl phosphate (Sigma Chemical Co., St. Louis, Mo.). This substrate is prepared at a strength approximately 1 mg/ml together with approximately 0.1 M glycine (pH 10.4), 1 mM zinc chloride, and 1 mM magnesium chloride. If the anti-epitope peptide antibody has bound to the epitope peptide coated to the plate, a colored product is formed. The optical density of the color can be ascertained by measuring the absorption at the proper wavelength for the particular color. The value of the optical density measured is directly proportional to the quantity of anti-epitope peptide antibody in the well sample.

Affinity Purification of Hybrid Epitope Peptide/Protein Molecules

Polyclonal or monoclonal antibodies with particularly low affinities for the epitope peptide are selected for use to purify the hybrid epitope peptide protein molecules. These antibodies are identified by the ability of soluble epitope peptide or moderate concentrations of salts (i.e., for example, 1 M NaCl) to inhibit binding of the antibodies to the epitope peptide-coated microtiter plate wells in the ELISA assays (see above) or by elution from an epitope peptide affinity column with a moderate concentration of salt. Antibodies with lower affinities for the epitope peptide are more useful for column elution purposes in that they permit release of the epitope peptide without having to use harsh eluting agents that can detrimentally damage the peptide.

The low affinity anti-epitope peptide antibody, identified and purified as in the manner set forth above, is coupled to a column gel. The unreacted sites of the gel are then blocked by use of a blocking agent, such as glycine ethyl ester. The antibody-coupled gel is washed extensively with a buffer such as borate buffered saline (BBS) or phosphate buffered saline (PBS). Next, the hybrid epitope peptide protein molecules are applied to the column and then the column rewashed with buffer. The hybrid epitope peptide protein molecules are specifically eluted from the column by competition with a high molar concentration free epitope peptide or moderate concentrations of salts, e.g., 1 M NaCl. The soluble epitope peptide substantially outcompetes the hybrid epitope peptide/protein molecules for the antibody coupled to the gel, whereas the 1 M NaCl disrupts ionic interactions between the antibody and the epitope peptide/protein molecule. As a result, a high yield of highly purified hybrid, epitope peptide protein molecules is obtained.

Separation of Mature Protein From Purified, Hybrid Epitope Peptide/Protein Molecules The hybrid molecules purified by the above discussed affinity chromatography procedure may be cleaved between the epitope peptide and the protein of interest. This is accomplished by first suspending the hybrid epitope peptide/protein molecules in buffer. Thereafter, a proteolytic enzyme or other chemical proteolytic agent that is specific for the amino acid residues composing the linking portion of the epitope peptide is added to the suspension. The enzyme may be coupled to a gel matrix to prevent contamination of the product solution with the enzyme. As discussed above, in some embodiments, it is preferable that a proteolytic enzyme or chemical proteolytic agent cleave the hybrid polypeptide between the adjacent amino acid residues of the linking portion of the epitope polypeptide and the protein of interest. Alternatively, in some embodiments the linker molecules are photocleavable, thus separation of the epitope peptide from the protein of interest is accomplished by the exposure to an appropriate wavelength of light. However, in other embodiments, it is desirable to maintain the linkage between the epitope polypeptide and the protein molecule.

After incubation with the proteolytic agent, the protein of interest is purified as follows. If the proteolytic agent is an enzyme attached to a gel matrix, the suspension is centrifuged and the pellet (containing the enzyme-gel conjugate) is discarded. The supernatant contains only the protein product, the cleaved epitope peptide and possibly small amounts of uncleaved peptide/protein molecule, in addition to buffer salts. In the case of chemical cleavage agents, there would be no gel centrifugation step, and the solution would contain a residual chemical agent and by-products of the chemical agent in addition to the protein product, epitope peptide and small amounts of uncleaved peptide/protein molecule.

Most of the above-mentioned contaminating substances are much smaller than the protein product and can be efficiently removed by simple means, such as gel filtration or dialysis. Only the uncleaved epitope peptide/protein molecule would remain to contaminate the protein product after such steps. To remove the peptide/protein molecule from the protein product, the mixture is passed over a second affinity column, which column has attached to it the same antibody specific for the epitope peptide as was used for removal of the peptide/protein molecule from the original production medium. The antibody binds the unwanted peptide/protein molecule, and the eluate from the column contains only the desired product protein, now free of all contaminants.

If a soluble enzyme is used for proteolytic cleavage, then the protein product may contain small amounts of the enzyme, which can be removed by passing the solution over an affinity column containing an immobilized substrate for the enzyme. The enzyme is thereby bound to the column and the protein of interest molecules allowed to pass through.

As noted above, some protein products will possess the desired enzymatic activity with the epitope peptide still attached thereto. As a consequence, the epitope peptide need not be cleaved from the protein molecule, thus the above described cleave and subsequent purification steps need not be performed.

Moreover, in situations in which the epitope peptide remains attached to the protein molecule, the linking portion of the epitope peptide is not needed. Instead, the epitope peptide can be composed solely of the antigenic residues. In this situation the construction and method of preparing the DNA expression vectors, detailed above, can be appropriately modified.

Experimental

EXAMPLE 1

Preparation of Recombinant Plasmid for *E. coli* Host Cell Transformation

Four oligomers in combination compose a translation initiation codon (ATG), bases coding for a ribosome binding site composed of the amino acid sequence and codons for the epitope peptide, said epitope, defined by the amino acid sequence: $X_N$-Asp-Asp-Asp-Asp-Lys (SEQ ID NO:23). In the epitope peptide, the sequence $X_N$ constitutes the epitope portion of the peptide (where $X_N$ represents amino acids and N is an integer defining length) while the sequence Asp-Asp-Asp-Asp-Lys (SEQ ID NO.:24) constitutes the protease cleavable linking portion of the epitope peptide. When the four synthetic oligomers are combined, they define a terminus compatible with a Hind III restriction endonuclease cleavage site. The other terminus of the synthetic fragment coincidentally corresponds to a Hind III restriction endonuclease cleavage site.

DNA coding for the selected protein, Interleukin 2 (IL-2), a regulatory hormone of the human immune system, for expression in transformed host cells, is prepared according to the procedures disclosed by Taniguchi et al., "Structure and Expression of a Cloned cDNA for human Interleukin 2," 302 Nature 305 (Mar. 24, 1983). The beginning terminus of the IL-2 DNA fragment is treated with linker molecules or by other appropriate method to form a blunt end corresponding to a T4-DNA polymerase cleavage site. The opposite end of the DNA fragment is appropriately treated to be compatible with Hind III cleavage site. The DNA coding for IL-2 also can be produced by well-known chemical synthesis techniques.

The four synthetic DNA oligomers are ligated to the IL-2 DNA to form a cointegrate fragment of approximately 730 base pairs (bp) in a 20 microliter reaction volume composed of 1 ul of each of the four synthetic DNA oligomers (20 nanograms (ng) each) with 5 ul of the IL-2 DNA fragments (200 ng). Also added are 2 ul of T4 DNA ligase and 2 ul 10×ligase buffer (0.66 M Tris {pH 7.5}, 50 mM magnesium chloride). Additionally added are 2 ul of 15 mM spermidine, 2 ul of 50 mM dithiothreitol, 2 ul of 1 mg/ml BSA and 1 ul of 20 mM adenosine triphosphate (ATP). The reaction is carried out by incubation overnight at 4° C.

The ligase mixture is electrophoresed on 1.2% agarose gel at 100 volts at room temperature. The region of the gel containing the 730 bp DNA fragments is excised and electroeluted from the gel. The DNA is extracted once with phenol:chloroform:isoamyl alcohol (25:25:1 volume). To the aqueouse phase, 2.5 volumes of 100% ethanol is added to precipitate the DNA. The solution is stored overnight at −20° C. and then centrifuged for 5 minutes at 10,000×g at room temperature, resulting in a pellet of the desired DNA product.

This 730 bp fragment has complementary ends that ligate to Hind III sites on the cloning vehicle plasmid.

The plasmid pYEJ001 (obtained from P. L. Biochemicals), as shown in FIG. 1, is prepared for ligation to the above prepared 730 bp fragment by digestion of the plasmid with Hind III restriction endonuclease, using 1 unit (U) of Hind III endonuclease per ug of DNA. The reaction includes 450 microliters of 1×Hind III buffer (70 mM Tris, (pH 7.4), 70 mM magnesium chloride, 0.6 M NaCl). This mixture is incubated at 37° C. for one hour.

The linearized DNA is then phosphatased to prevent self-ligation with 45 ul of 10.times.CIP buffer (0.5M Tris [pH 9.0], 10 mM magnesium chloride, 1 mM zinc chloride, 10 mM spermidine) and 1 ul of calf intestinal phosphatase (30 U). The mixture is incubated at 37° C. for 30 minutes and then extracted once with phenol:chloroform:isoamyl alcohol (25:25:1, vol.) as above. To the aqueous phase 2.5 volumes (relative to the aqueous phase) of 100% ethanol are added and the resulting mixture is stored at −20° C. overnight. The mixture is then centrifuged at 10,000×g for 5 minutes at 22° C., yielding a pellet. The pelleted DNA is electrophoresed on a 0.7% agarose gel at 100 volts at 22° C. for 2 hours.

Digestion of plasmid pYEJ001 produces two DNA fragments, one of 3,273 bp and one of 787 bp. The larger fragment, containing sequences encoding the tetracycline and ampicillin phenotypic markers, a lac operator and synthetic promoter, is isolated by electroelution and then extracted once with phenol:chloroform:isoamyl alcohol (25:25:1, vol.). To the aqueous phase are added 2.5 volumes of 100% ethanol and then the solution is stored at −20° C. overnight. The mixture is next centrifuged at 10,000×g for 5 minutes at 22° C. and the desired product is contained in the pellet.

The previously ligated epitope peptide oligomers/IL-2 fragment is ligated to the above isolated 3,273 bp fragment of the pYEJ 001 plasmid by combining 2 microliters of the pYEJ001 3273 bp fragment (100 ng) with 500 ul of the combined epitope peptide/IL-2 fragment (660 bp) prepared above, (100 nanogram) together with 2 ul of 10× ligase buffer (0.66M Tris {pH 7.5}, 50 mM magnesium chloride), 2 ul of 50 mM dithiothreitol, 2 ul of 50 mM spermidine, 2 microliters of 1 mg/ml BSA, 1 ul of 20 mM adenosine triphosphate, 3 ul $H_2O$ and 1 ul of T4 DNA ligase. The mixture is incubated at 15° C. overnight.

The resulting recombinant plasmid, is then transformed into E. coli strain RR1 using standard transformation techniques, such as disclosed in Maniatis et al, Molecular Cloning: A Laboratory Manual, Cold Spring Harbor Laboratory (1982). The host cells are grown in culture and then lysed. Plasmids from the host cells that have undergone transformation are checked for correct orientation of the foreign genes (cointegrate epitope peptide oligomers/IL-2 fragment) within the plasmid.

EXAMPLE 2

Production of Monoclonal Antibody

BALB/c mice are initially immunized subcutaneously in the right and left hind legs with 100 ug of epitope peptide. Prior to immunization, the epitope peptide is prepared as an emulsion by mixing 4 mg of the epitope peptide in 2 ml of double distilled sterile water and then adding 2 ml of complete Freund's adjuvant (Difco Laboratories, Detroit, Mich.). After the initial immunization, the mice are rechallenged bi-monthly with 100 mg of epitope peptide in incomplete Freund's adjuvant.

After the second immunization and each immunization thereafter, the animals are bled retro-orbitally with a sterile pipet. The collected blood is allowed to clot for the 30 minutes at room temperature and then the serum prepared by centrifugation of the clotted blood for 10 minutes at 450×g. This serum is tested for anti-epitope peptide antibody response by use of ELISA assay, as detailed previously. The ELISA assays are repeated after each subsequent immunization until mice are identified which produced significant serum titer against the epitope peptide. Once a high serum titer is detected, the animals were given epitope peptide in saline in intravenous injection.

Three to four days later the animals are sacrificed by cervical dislocation. The spleens from these animals are harvested and single cell suspensions prepared therefrom. The spleens are cultured in Click's medium (Altick Associates, Hudson, Wis.). The medium is supplemented with 10% (vol./vol.), heat-inactivated fetal calf serum (FCS), 300 ug/ml of fresh L-glutamine, 50 ug/ml of gentamycin, 50 U/ml of penicillin, 50 ug/ml of streptomycin, 25 mM Hepes buffer and 16 mM $NaHCO_3$ (complete Click's medium).

Fusion is achieved by mixing approximately $20\times10^6$ spleen cells with approximately $10\times10^6$ NS1 murine myeloma cells in a 15 ml conical centrifuge tube. The cell mixture is pelleted by centrifugation for 10 minutes and 250×g and the supernate discarded. One ml of a solution of 40 percent (weight/volume) of PEG diluted in complete Click's medium is then added to the cell pellet in dropwise manner. Thereafter, 10 ml of complete Click's medium is added to the centrifuge tube over a 2 minute period and the cell pellet gently resuspended. Next, the mixture is centrifuged for 5 minutes at 250×g and the supernate discarded to complete the fusion process.

Anti-epitope peptide antibody is derived from the fused cells by resuspending the resulting cell pellet in 40 ml of complete Click's medium. The unfused myeloma driver cells (NS1), double NS1 hybrids, unfused spleen cells and double spleen cell hybrids are prevented from proliferating by the addition to the medium of approximately 1.36 mg/ml of hypoxanthene, 0.00176 mg/ml of aminopterin and 0.388 mg/ml of thymidine (complete Click's HAT medium). Also, approximately $120\times10^6$ BALB/c mice thymidine cells are added as filler cells. The entire cell suspension are then divided into 200 microliter aliquots in flat-bottom microtiter plates (No. 3596 Costar Inc., Cambridge, Mass.). The cultures are all maintained at approximately 37° C. in a humidified atmosphere of 7% $CO_2$ in air. After from 7 to 10 days of culture, supernates from wells containing viable hybrid cells are tested by ELISA for the presence of anti-epitope peptide antibody.

The invention claimed is:

1. A composition, comprising:
   a) a first nucleic acid sequence encoding for a protein of interest or portion thereof; and
   b) a second nucleic acid sequence encoding a translation initiation codon, a p53 epitope, wherein said p53 epitope consists of the amino acid sequence of SEQ ID NO.:25, and a cleavable linker, wherein said first nucleic acid sequence is ligated to said second nucleic acid sequence.

2. The composition of claim 1, wherein said cleavable linker, upon expression of said second nucleic acid sequence, is attached to the N-terminal end of said protein of interest.

3. The composition of claim 1, wherein said cleavable linker, upon expression of said second nucleic acid sequence, is attached to the C-terminal end of said protein of interest.

4. The composition of claim 1, wherein x of SEQ ID NO.:25 is selected from the group consisting of H, Y, G, N, F, D and T.

5. A vector comprising the composition of claim 1.

6. A cultured host cell comprising the vector of claim 5.

7. The host cell of claim 6, wherein the host cell is *E. coli*.

8. The cultured host cell of claim 6, wherein the host cell is a mammalian cell.

9. A composition, comprising two contiguous nucleic acid sequences:
   a) a first nucleic ac sequence encoding for a protein of interest or portion thereof; and
   b) a second nucleic acid sequence encoding a translation initiation codon, a p53 epitope, wherein said p53 epitope consists of the amino acid sequence of SEQ ID NO.: 25, wherein x of SEQ ID NO.: 25 is selected from the group consisting of H, Y, G. N, F, D and T, and a cleavable linker, wherein said first nucleic acid sequence is ligated to said second nucleic acid sequence.

10. A vector comprising the composition of claim 9.

11. A cultured host cell comprising the vector of claim 10.

12. A composition, consisting of:
   a) a first nucleic acid sequence encoding for a protein of interest or portion thereof; and
   b) a second nucleic acid sequence encoding a translation initiation codon, a p53 epitope, wherein said p53 epitope consists of the amino acid sequence of SEQ ID NO.:25, and a cleavable linker, wherein said first nucleic acid sequence is linked to said second nucleic acid sequence.

13. A composition, consisting of two contiguous nucleic acid sequences:
   a) a first nucleic acid sequence encoding for a protein of interest or portion thereof; and
   b) a second nucleic acid sequence encoding a translation initiation codon, a p53 epitope, wherein said p53 epitope consists of the amino acid sequence of SEQ ID NO.: 25, wherein x of SEQ ID NO.: 25 is selected from the group consisting of H, Y, G, N, F, D and T, and a cleavable linker, wherein said first nucleic acid sequence is linked to said second nucleic acid sequence.

\* \* \* \* \*